US007410904B2

(12) United States Patent
Stasiak et al.

(10) Patent No.: US 7,410,904 B2
(45) Date of Patent: Aug. 12, 2008

(54) SENSOR PRODUCED USING IMPRINT LITHOGRAPHY

(75) Inventors: James Stasiak, Lebanon, OR (US); Kevin Peters, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 894 days.

(21) Appl. No.: 10/423,063

(22) Filed: Apr. 24, 2003

(65) Prior Publication Data
US 2004/0214447 A1 Oct. 28, 2004

(51) Int. Cl.
*H01L 21/311* (2006.01)
(52) U.S. Cl. .................. 438/700; 438/691; 216/44; 216/52
(58) Field of Classification Search ............ 216/40, 216/44, 52, 53; 438/691, 700, 735; 249/115, 249/118; 425/174; 355/67, 72, 73, 75; 101/3.1
See application file for complete search history.

(56) References Cited

U.S. PATENT DOCUMENTS

| 5,646,464 | A | | 7/1997 | Sickafus |
| 5,772,905 | A | * | 6/1998 | Chou ................ 216/44 |
| 5,925,259 | A | * | 7/1999 | Biebuyck et al. ......... 216/2 |
| 6,128,214 | A | | 10/2000 | Kuekes et al. |
| 6,190,929 | B1 | * | 2/2001 | Wang et al. .............. 438/20 |
| 6,197,399 | B1 | | 3/2001 | Naito et al. |
| 6,294,450 | B1 | | 9/2001 | Chen et al. |
| 6,314,019 | B1 | | 11/2001 | Kuekes et al. |
| 6,334,960 | B1 | * | 1/2002 | Willson et al. ............ 216/52 |
| 6,365,059 | B1 | | 4/2002 | Pechenik |
| 6,432,740 | B1 | | 8/2002 | Chen |
| 6,518,156 | B1 | | 2/2003 | Chen et al. |
| 6,843,899 | B2 | * | 1/2005 | Ufer ...................... 204/400 |
| 6,849,558 | B2 | * | 2/2005 | Schaper ................... 438/758 |
| 2002/0117659 | A1 | | 8/2002 | Lieber et al. |
| 2003/0003775 | A1 | | 1/2003 | Chen |

FOREIGN PATENT DOCUMENTS

WO    WO99/64642    12/1999

OTHER PUBLICATIONS

Cui et al., Nanowire Nanosensors for Highly Sensitive and Selective Detection of Biological and Chemical Species, Aug. 17, 2001, Science, vol. 293, pp. 1289-1292.*
Wolf et al., Silicon Processing for the VLSI Era, 1986, Lattice Press, vol. 1, pp. 120, 514.*
Wolf, Silicon Processing for the VLSI Era, 2002, Lattice Press, vol. 4, pp. 501-502.*
Bailey et al., "Step and Flash Imprint Lithography: An Efficient Nanoscale Printing Technology", Journal of Photopolymer Science and Technology, 2002, pp. 481-486, vol. 15, n.3.
Johnson et al., "Advances in Step and Flash Imprint Lithography", Proc. of SPIE, Lithographic Technologies VII, Feb. 2003, pp. 197-202, vol. 5037, Austin, TX, USA.

(Continued)

*Primary Examiner*—Kin-Chan Chen

(57) ABSTRACT

The disclosure relates to a process including depositing an imprintable layer on a substrate. The imprintable layer is imprinted into the pattern of an imprint-fabricated ribbon. The pattern from the imprintable layer is transferred to the substrate to be used to fabricate the imprint-fabricated ribbon.

52 Claims, 7 Drawing Sheets

OTHER PUBLICATIONS

Chou et al., "Sub-10 nm imprint lithography and applications", Journal of Vacuum Science and Technology B, Nov. 1997, pp. 2897-2904.

Guo et al., "Nanoscale silicon field effect transistors fabricated using imprint lithography", Applied Physics Letters, American Inst. of Physics, Sep. 1997.

Schift et al., "Chemical nano-patterning using hot embossing lithography", Micrelectronic Engineering, Elsevier Publishers, Amsterdam, NL, Jul. 2002, pp. 423-428, vol. 61-62.

Chou et al., "Imprint Lithography with 25-Nanometer Resolution", American Association for the Advancement of Science, Apr. 1996, pp. 85-87, vol. 272, USA.

Hoff et al., "Nanoscale Protein Patterning by Imprint Lithography", Nano Letters/American Chemical Society, Apr. 2004, pp. 853-857, vol. 4, No. 5.

International Search Report for PCT Application No. PCT/US2004/012357 (filed Apr. 23, 2004), Jan. 2005.

Cui et al., "Nanowire Nanosensors for Highly Sensitive and Selective Detection of Biological and Chemical Species", Science Magazine, Aug. 2001, vol. 293, pp. 1289-1292.

Michel et al., "Printing meets lithography: Soft approaches to high-resolution patterning", IBM Research and Development, Sep. 2001, vol. 45, No. 5, pp. 697-719.

* cited by examiner

SENSOR PRODUCED USING IMPRINT LITHOGRAPHY

TECHNICAL FIELD

This invention relates to sensors, and more particularly to sensors produced by imprint lithography.

BACKGROUND

Prior art nano-scale sensors are used in a large number of applications, and have been found particularly suited in the fields of chemical and/or biological sensing and analysis. Such prior art nano-scale sensors are typically produced individually by non-repetitive (and therefore inefficient) methods that do not use batch processing manufacturing techniques. Prior art nano-scale sensors find application in such analysis techniques as gas chromatography, ionically coupled plasma atomic analysis (ICPAA), wet chemical analysis, PCR (polymerase chain reaction), mass spectroscopy via laser volatilization, electrophoresis, and fluorescent tagging methods, to name a few.

Chemical and/or biological sensing and analysis traditionally requires a long time to obtain meaningful data, involves remote or cumbersome equipment, requires large sample sizes, demands highly trained users, and involves significant direct and indirect costs. Direct costs relate to the labor, procedures, and equipment required for each type of analysis. Indirect costs partially accrue from the delay time before actionable information can be obtained, e.g., in medical analyses or in the monitoring of chemical processes. Indirect costs of certain chemical or biological analyses can outweigh the direct costs.

Certain embodiments of biological and/or chemical analysis equipment use loose tubular wires or tubes whose electrical resistance is measured using a two terminal configuration. The term "loose" indicates that the wire or tube is not initially secured to the substrate and so must subsequently be affixed to it.

Advantages of the loose tube type of construction of sensors are simplicity and ease of laboratory demonstration. Minute wires can also be deposited directly on a substrate by a chemical vapor deposition (CVD) process, which is also time consuming and expensive. However, it is difficult and expensive to manufacture loose nano-scale wires or tubes in a sufficiently reproducible way for useful sensing applications.

Some analytical techniques also require arrays of sensors to sense some parameter over a two-dimensional or three-dimensional configuration. It is difficult to fabricate loose tubes or wires into arrays in large quantities, especially when the tubes or wires are in the nano-scale. Typically, each wire or tube for sensor within the array is individually fabricated, which is time consuming and expensive.

There is therefore a need for a technique for manufacturing nano-scale wires and tubes in a less expensive, more reproducible, and more production-friendly manner than permitted by present-day techniques.

BRIEF DESCRIPTION OF THE DRAWINGS

The same numbers are used throughout the drawings to reference like features and components.

DETAILED DESCRIPTION

Figure 1:
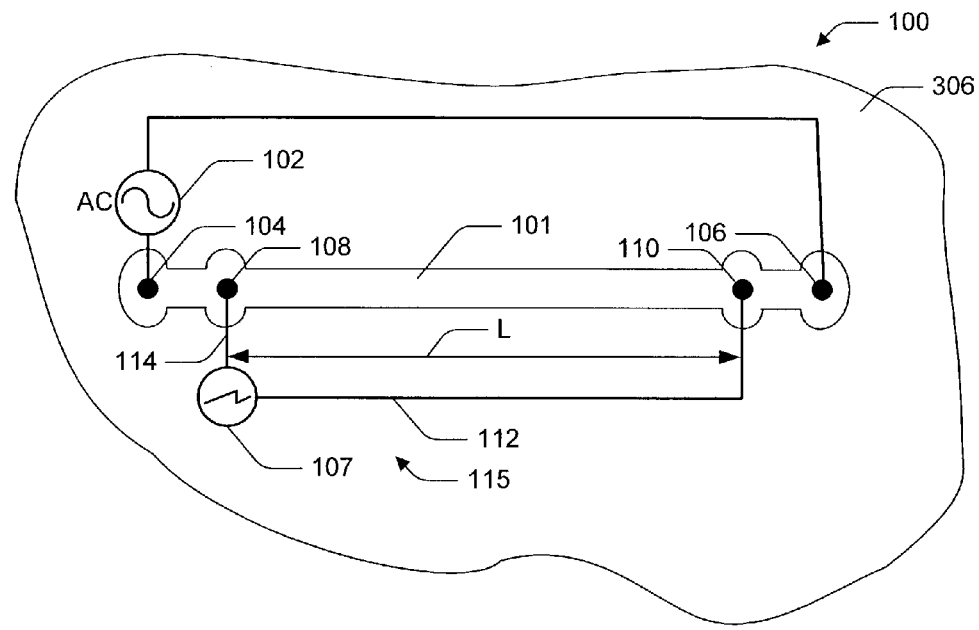
FIG. 1 illustrates a top view of one embodiment of an imprint-fabricated ribbon.

The following describes different embodiments of an imprint-fabricated sensor 100 that can be produced using an imprinting or stamping process described herein which is referred as imprint lithography (IL). IL techniques can fabricate imprint-fabricated sensors 100 in the nano-scale, the meso-scale, the micro-scale, the macro-scale, other scales, and/or in combinations of these scales. Certain embodiments of the imprint-fabricated sensor can be used as a platform in a broad variety of chemical and/or biological sensing applications in which detection can be monitored electrically.

One aspect of chemical and/or biological sensing applications for imprint-fabricated sensors as described in this disclosure is associated with functionalization. With functionalization, the surface of the imprint-fabricated sensor 100 is treated, coated, contoured, roughened, or otherwise configured so that certain species are attracted, repelled, and/or affixed to the surface of the imprint fabricated sensor once the surface of the imprint-fabricated sensor is exposed to an analyte. As such, functionalization can result in the surface of the imprint-fabricated sensor being engineered to promote or inhibit the adsorption of certain species. One embodiment of functionalization involves the chemical and/or biochemical coating of the imprint-fabricated sensor by a molecular-scale layer of probe substances. The probe substance promotes the surface adsorption or reaction of specific target molecules in preference to other species. As a result of the target molecule being reacted with during functionalization, the electronic or magnetic properties of the imprint fabricated sensor 100 are altered when in the presence or absence of the target species. This altering of the electronic or magnetic properties can be sensed by electronic sensing equipment (often computer-based) whose operation and structure is generally known and will not be further described. In one embodiment, the functionalized is by fabrication of a dielectric layer such as silicon oxide or nitride that can be readily protonated or deprotonated to provide for the detection of protons in solution.

Certain embodiments of the imprint-fabricated sensors 100 (especially those formed in the nano-scale) can provide extremely high sensitivity. Imprint fabricated sensors fabricated in the nano-scale, for example, are sensitive enough to detect the effects of even single molecules. Such imprint-fabricated sensors 100 (e.g., those used in such biological or chemical fields as for functionalization) can provide more rapid time-to-data, more meaningful information from smaller sample sizes, simplified usage, and/or lower total cost. The biological or chemical imprint-fabricated sensor 100 appears to have particular applicability in high-sensitivity applications as a result of the high surface-area-to-volume ratio involved. However, applications demanding lesser sensitivity may also be well served using imprint-fabricated sensors 100 produced using the associated IL technologies. An attribute of imprint-fabricated sensors is the ability to co-fabricate nano-scale and much larger devices simultaneously so that, in the ensemble, the resulting devices have similar properties and sensitivities and can be compared effectively.

IL can provide distinct or patterned lines onto the surface of a substrate using an imprinting process. Such distinct or patterned lines can be imprinted in nano-scale, micro-scale, macro-scale, or a combination of these. In this disclosure, the term "imprinted" or "stamped" lines pertain to lines that are fabricated using an IL process. Subsequent processing is usually performed on the a substrate that has been imprinted or stamped to produce imprinted lines. Such imprinted lines can also be used as electrical transducers for chemical absorption. An example of an improved chemical and/or biological sensor is described that transduces chemical surface adsorption to an electrical response such as resistance.

This disclosure describes different embodiments of imprint-fabricated ribbons 101 that exploit the high sensitivity, selectivity, and resolution of unattached "free" nanowire sensing techniques. A systematic method for patterning and organizing the arrays of the imprint-fabricated ribbons 101 using IL is provided. Furthermore, the method described provides a technique to tailor and tune the electrical and chemical properties of the imprint-fabricated ribbons 101, thereby improving their performance and permitting a more controllable and manufacturing-friendly process. The advantages provided by many embodiments of the imprint-fabricated sensor 100 lead to useful, manufacturable imprint-fabricated ribbon arrays.

Electrical-based elements, including imprint-fabricated ribbons 101, can be physically contoured to specifically attract specific and predetermined areas of a surface patterned for functionalization with particular target species supported in analytes. Suitable functional groups include, but are not limited to chemical/biological groups of interest, such as thiols, amines, silanols, alcohols, sugars, Lewis acids and bases, dipoles, nucleic acids, peptides, etc. (perhaps in various combinations). Imprint-fabricated ribbons 101 are particularly suitable for chemical and/or biological functionalization by attracting the target species to an exposed exterior surface.

The imprint-fabricated ribbons 101 can be patterned to provide functionalization. One description of functionalization is described in U.S. patent application Ser. No. 2002/0117659, filed Aug. 29, 2002 by Lieber et al. (incorporated herein by reference). Chemical and/or biological changes associated with the imprint fabricated ribbons 101 (that are enhanced or retarded based on the configuration of the imprint fabricated ribbons) can be used to modulate electric current passing through the imprint fabricated ribbons 101. Presence of the analyte can change the electrical properties of the imprint fabricated ribbons 101 through electrocoupling with a binding agent of the imprint-fabricated ribbons 101. The imprint fabricated ribbons 101 can be coated with a specific reaction entity, binding partner or specific binding partner, chosen for its chemical or biological specificity to a particular analyte. Positioning the reaction entity at a relative distance (preferably within the nanometer or low tens of nanometers) relative to an external surface of the imprint-fabricated ribbons 101 causes a detectable change in the imprint fabricated ribbons.

Figure 2:
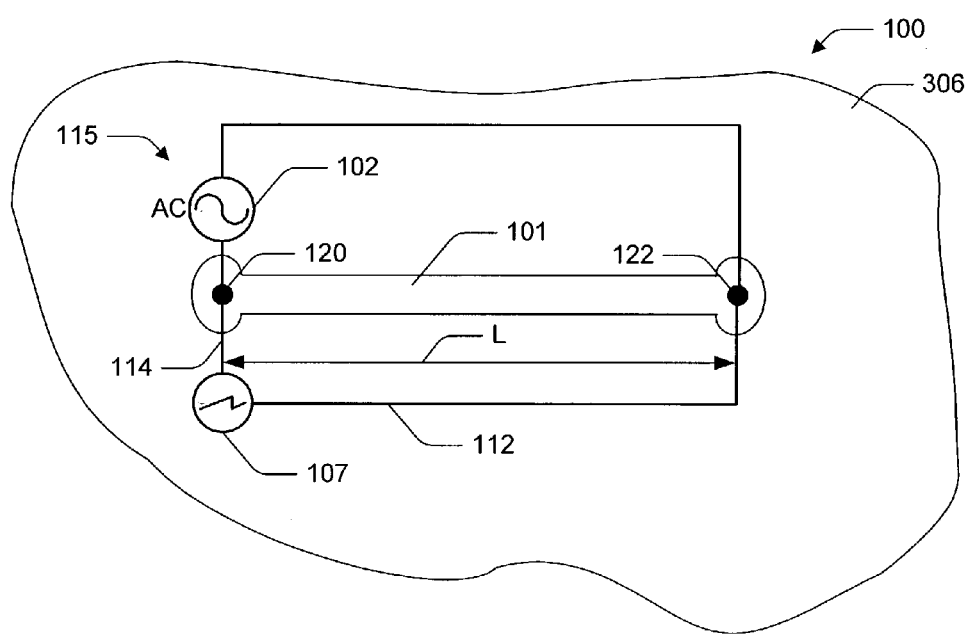
FIG. 2 illustrates a top view of another embodiment of the imprint-fabricated ribbon.

Two embodiments of the imprint-fabricated sensor 100 are shown in FIGS. 1 and 2. This disclosure describes a variety of associated techniques to fabricate an imprint-fabricated ribbon 101 that can be used in the imprint-fabricated sensor 100. As such, a method of making high-sensitivity biological, chemical, or bio-chemical sensors in large quantities using IL as described in this disclosure, can be used to produce many embodiments of the imprint-fabricated ribbon 101.

This disclosure applies to imprint-fabricated ribbons 101 having a variety of configurations. An imprint-fabricated ribbon 101 can be considered a ribbon-shaped strip having any desired cross-sectional aspect ratio in one or two substantially orthogonal dimensions, and which is formed from a semiconductor material, a conductor material, or a composite material. The imprint-fabricated ribbon can be elongated in a third orthogonal direction to provide the path of the ribbon. A rectangular cross-section imprint-fabricated ribbon can be designed that has a greater thickness dimension than its width, if desired. The aspect ratio of a ribbon is the height divided by the width of the ribbon. However, other configurations are feasible, and are considered as part of this disclosure.

The embodiments of imprint-fabricated ribbon shown in FIGS. 1 and 2 are substantially rectangular in cross-sectional configuration, as implied by the use of the term "ribbon". This substantially rectangular configuration compares to the circular or oval cross-section of many prior-art configurations of sensors. The substantially rectangular configuration of the imprint-fabricated ribbon may be recognized more generally as trapezoidal where the lateral walls are actually angled inward or outward from being perpendicular to the base. Such angling can occur as a result of fabricating the imprint-fabricated ribbon, especially in the nano-scale. As such, the imprint-fabricated ribbon thereby can deviate from a strict rectangular cross-sectional shape. It is also understood that the bounding surfaces have, to some extent, irregularities and even defects such as roughness, occlusions, inclusions, ridges, faceting, etc. Such deviations of the imprint-fabricated ribbon from the substantially rectangular cross-sectional configuration are understood to be dependent on details of the process and materials employed. Being substantially rectangular, an imprint-fabricated ribbon 101 that is wider than its thickness dimension (has a lower aspect ratio) provides more surface area with which the analyte can react than does the imprint-fabricated ribbon that is substantially square in cross-section (having an aspect ratio of approximately one). An imprint-fabricated ribbon 101 is particularly adaptable to certain applications. For certain applications such as imprint-fabricated sensors, imprint-fabricated ribbons provide an important degree of independent control of the ribbon height, width, and length as well as an ability to co-fabricate ribbons of varying width, height, length, surface feature, and/or other ways. Alternatively, the geometrical form and aspects of the ribbon material composition itself can be varied by altering the dopant species and dopant concentration, to name a few. Such control and flexibility in design is desirable and is afforded by certain concepts of the present disclosure.

This disclosure describes different embodiments of imprint-fabricated sensors and/or features that can be fabricated within the nano-scale, micro-scale, macro-scale, meso-scale, or other dimensional ranges. Such dimensional terms as "nano-scale", "micro-scale", "macro-scale" and "meso-scale" are applied to electronic circuits and electronic devices in which at least one electronic device has at least one dimension that is in the respective "nano-scale", "micro-scale", "macro-scale", or "meso-scale" range. However, all portions of electrical circuits do not have to be configured within the same scale. For example, the sensor structure itself may be fabricated in the nano-scale range, while the electrical supply circuitry may be fabricated in some larger range.

Imprint-fabricated sensors 100 can be fabricated with a variety of cross-sectional aspect ratios using IL, which is important since altering the aspect ratio of the imprint-fabricated ribbon changes its sensing characteristics. For instance, an imprint-fabricated ribbon 101 with increased surface area allows more electrons and/or holes to flow through the ribbon during an analysis. Altering the aspect ratio of imprint-fabricated sensors can also alter the surface area exposed to the analyte during a sensing operation. The surface area of the imprint-fabricated ribbons 101 that contacts the analyte controls the areas of chemical reaction, and therefore largely determines the functionalization operation. The relationship between the size of the analyte and the dimension of the imprint-fabricated ribbon 101 therefore is quite important.

In certain embodiments, the imprint-fabricated sensor 100 detects charged particles that are proximate to the sensing surface, and which can be absorbed onto that surface. The charged particles are attracted to the surface of the imprint-fabricated ribbon 101 by virtue of an electronic charge or dipole, or a change in charge. By accurately sensing the charged particle, the imprint-fabricated sensor 100 can provide a precise indication of the particles within any chemical or biological analyte or sample, whether the analyte or sample is a gas, a liquid, or is dry.

FIGS. 1 and 2 illustrate two embodiments of the imprint-fabricated ribbon 101 that are biased to sense proximate charged particles. An electrical circuit 115 that biases the imprint-fabricated ribbon 101 in a four-point resistance measurement or a two-point resistance measurement is shown in FIGS. 1 and 2.

FIG. 1 illustrates a four-point resistance measurement across an imprint-fabricated ribbon 101 in which the output from a voltage or current source 102 existing across two outer electrical contacts 104, 106 is measured across two inner electrical contacts 108, 110. The voltage or current source 102 could be either AC or DC biased across the outer two electrical contact points 104, 106. An electric potential meter such as a voltmeter 107 is applied across two inner electrical contacts 108, 110.

As such, the imprint-fabricated sensor 100 can be viewed as the imprint-fabricated ribbon 101 having the current source 102 at two outer electrical contacts 104, 106 that force a current through the imprint-fabricated ribbon 101. The two inner electrical contacts 108, 110 are located somewhere between the outer two electrical contacts 104 and 106. Leads 112, 114 of the voltmeter 107 are separated by a known distance L on the imprint-fabricated ribbon 101, as determined by the distance between the two inner electrical contacts 108, 110. The voltmeter 107 detects the voltage or current at the two inner contacts during the sensing event.

By knowing the current and the measured voltage of the imprint-fabricated ribbon 101, its resistance can be precisely extracted using Ohm's law. By ensuring that the current is constant between the two outer electrical contacts 104, 106, Ohm's law can calculate the resistance between the two inner contacts. In one embodiment, each one of the two inner electrical contacts 108, 110 is in quite close proximity to respective ones of the two outer electrical contacts 104, 106.

By biasing imprint-fabricated ribbons 101 with a known low frequency alternating current, a locking detection can also be performed where the effects of electronic noise are removed from the overall measurements. As such, the effects of noise can be extracted from the total received signal for the sensing event. Reducing the effects of noise improves the accuracy of the analysis.

Another embodiment of the electrical circuit of the imprint-fabricated sensor 100 is illustrated in FIG. 2, and includes two electrical contacts 120, 122. The FIG. 2 embodiment is a two-point resistance measurement in which a forced current across a pair of electric contacts 120, 122 is sensed at a voltmeter 107 connected across the same pair of electric contacts 120, 122. Inner electrical contact 108 and outer electrical contact 104 in the FIG. 1 embodiment can be structurally made to be, and functionally considered as, a unitary electrical contact 120 of FIG. 2. Additionally, inner electrical contact 110 and outer electrical contact 106 in the FIG. 1 embodiment can be viewed as forming a unitary electrical contact 122 of FIG. 2. With the two-point resistance measurement as shown in FIG. 2, there is some resistance due to the junction between the electrical contacts and the imprint-fabricated ribbons 101 themselves. This contact resistance is included in the total signal, and makes isolating the sensed signal from the noise more challenging. Using the four-point resistance technique as shown in FIG. 1 tends to decrease the effects of the contact resistances.

The configurations displayed in FIGS. 1 and 2 include only one single imprint-fabricated ribbon 101. However, more sophisticated or complex arrays of imprint-fabricated ribbons 101 are within the intended scope of the present disclosure as described relative to FIG. 6.

The imprint-fabricated ribbons 101 of the imprint-fabricated sensors 100 include an electrically conductive material. Such electrically conductive materials include one or more metals such as platinum, beryllium, aluminum, palladium; metallic alloys; a ceramic such as indium tin oxide, vanadium oxide, or yttrium barium copper oxide; an electrically semi-conductive material such as silicon, diamond, germanium, gallium arsenide, cadmium telluride, zinc oxide, silicon carbide, tin oxide, indium tin oxide; and/or other elemental, binary, and multi-component materials. As such, virtually any electrically conductive material that can be formed to the imprint-fabricated ribbons are within the intended scope of the imprint-fabricated sensors 100.

When the imprint-fabricated ribbon 101 is electrically biased (either using a voltage or current potential gradient), a charge imbalance is produced when any charged particle is brought close to the surface of the imprint-fabricated ribbon 101. This charge imbalance then modifies the current flowing through the imprint-fabricated ribbon 101, and this modification is used to detect the presence of, proximity of, and/or quantity of charged particles during the sensing event.

Figure 6:
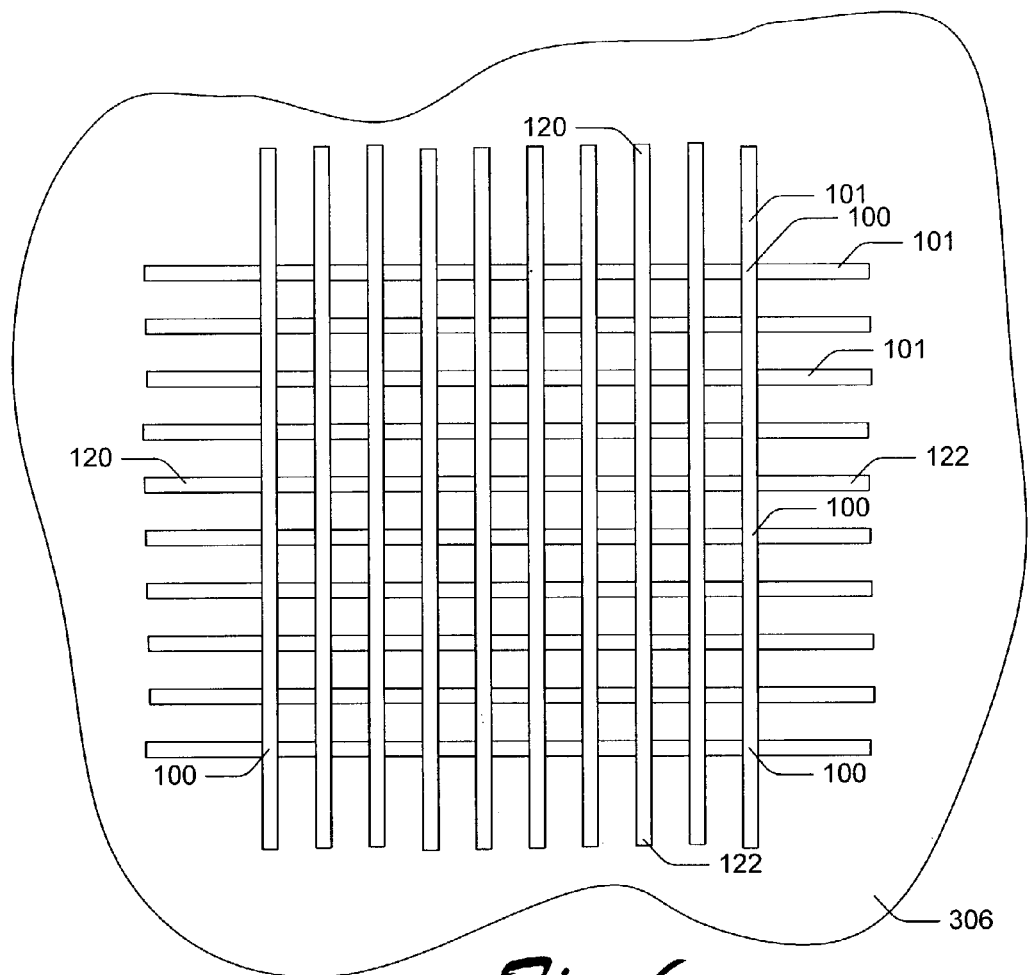
FIG. 6 illustrates one embodiment of an array of imprint-fabricated ribbons.

Each imprint-fabricated ribbon 101 in different embodiments of an array can have similar or different cross-sectional dimensions in order to better detect different chemical and/or biological species. In one embodiment, an array of imprint-fabricated ribbons 101 will include different widths, thicknesses, etc. The array of imprint-fabricated ribbons can have different dimensions to differentiate one species from another similar species that may be contributing to background noise signals. Alternatively, multiple imprint-fabricated ribbons can be fabricated to have the same cross-sectional configuration as, for example, an array as illustrated in FIG. 6. Certain ones of the individual imprint-fabricated ribbons might be provided with different dopants, surface preparations, or functionalization techniques.

The imprint-fabricated ribbons 101 may be formed, preferably having at least one cross-sectional nano-scale dimension, compared to picoscale or to some other larger dimension. This provides more precise sensing in that the effects of a single charged particle can be more accurately sensed. Although not having a nano-scale dimension does not preclude the utility of this method of manufacture or its application to imprint-fabricated sensors. Additionally, a large surface area to volume ratio can be provided even with relatively small imprint-fabricated ribbons 101, which further enhances the sensitivity of single charged particles. By using an imprint-fabricated ribbon 101 of at least one nanometer dimension, unprecedented selectivity and sensitivity can be achieved compared to imprint-fabricated ribbons having larger dimensions.

The imprint-fabricated ribbon 101 concepts can produce a large number of practical devices and arrays. In general, integrated circuit technology concepts have historically produced a large number of very small-dimensioned devices. Certain techniques developed for integrated circuit fabrication (such as IL substrate stamping techniques and the use of Silicon-On-Insulator (SOI) substrates) can also be utilized during the fabrication of the imprint-fabricated sensors 100. Alternatively, solid semiconductor substrates can be used in certain embodiments of the present disclosure.

IL is a relatively recently developed lithography process that is included within the area of soft lithography. In the last few years, people have looked at IL's ability to create nano-scale features. IL is a stamping or imprinting process by which a pattern in a mold or template is stamped on to a material (e.g., a polymer) that had been deposited on a substrate. In this manner, the desired shape or topographical features are rapidly formed in the deposited material. Materials such as a metal are deposited onto the substrate 306 to form an electrically conductive circuit. Forming such electrically conductive circuits using IL is desirable since it creates and/or replicates these nano-scale structures in semiconductor or conductor materials by repetitive stamping. Such stamping or imprinting can result in the full-scale, production quantity, fabrication of imprint-fabricated sensors that have high resolution, sensitivity, and selectivity. IL of sensors can be easily applied to certain substrates within an integrated-circuit configuration.

While other technologies can be used to create nano-scale features (e.g. using electron-beam, etc), such technologies are untenable as a high-volume production manufacturing technique because they are time consuming and the equipment is expensive. IL technology allows small features to be replicated and produced. SOI technology provides for sufficiently thin semiconductor active layers to be fabricated to allow relatively thin devices to be placed on the substrate 306 as illustrated in FIG. 3.

IL of one, a plurality of, or an array of imprint-fabricated ribbons 101 includes depositing an extremely thin conductor or semiconductor active layer 302 on to a substrate 306, using a technology such as SOI. In an alternate embodiment (not shown), the substrate 306 is a solid semiconductor substrate. An electrical insulator layer 304 is interspaced between the conductor or semiconductor active layer 302 and the substrate 306. The relative thickness of 302, 304, and 306 are not drawn to scale in FIG. 3. The conductor or semiconductor active layer 302 can be a deposited in a wide variety of thickness that are extensible down to one or a few atoms thick. In one illustrative embodiment, the semiconductor active layer 302 is 50 nanometers (nm) thick or less and the electrical insulator layer 304 is 350 nm thick. During fabrication, a plurality of layers may be deposited on top of the substrate. Following the deposition of the layers on the substrate, the substrate is cut (or sawed) into a plurality of chips as is generally known in the semiconductor industry. In this disclosure, the term "substrate" applies to the original substrate, or each one of those chips cut from the substrate.

The conductor or semiconductor active layer 302 is patterned (by suitable imprinting/stamping, deposition, and/or etching) to form the imprint-fabricated ribbons 101 in to the desired configuration. One or more of the deposited layers are then etched to pattern the desired shapes of the imprint-fabricated ribbon 101. In SOI substrates 306, the handle 317 (i.e., thick silicon layer) forming the base of the substrate. The handle 317 acts to support the insulator and the active silicon layer. The substrate of SOI wafers includes both an oxide insulator layer (also known as the buried oxide layer) and a very thin silicon layer deposited on top of the insulator.

Figure 3:
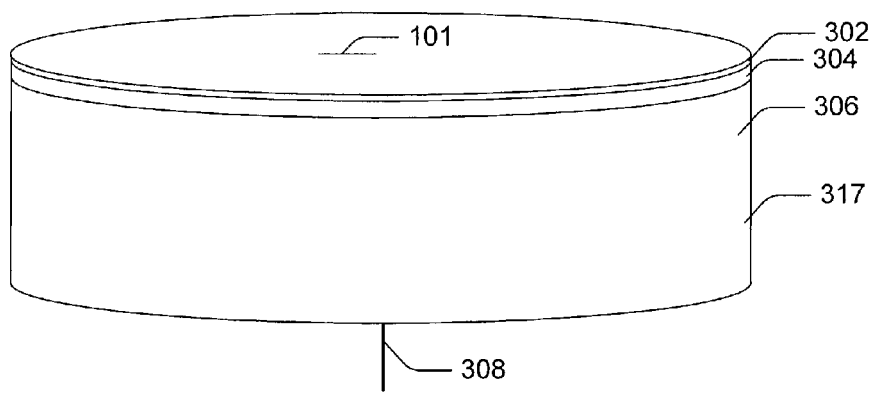
FIG. 3 illustrates a perspective view of a silicon-on-insulator (SOI) substrate that can be configured to have one or more imprint-fabricated ribbons of the type illustrated in FIGS. 1 and 2 fabricated thereupon.

While the conductor or semiconductor active layer 302 is illustrated in FIG. 3 as being continuous, certain portions of the conductor or semiconductor active layer 302 can be removed during the patterning process. In one embodiment, the only portions of the conductor or semiconductor active layer 302 that remain following fabrication (as described relative to FIGS. 5a, 5b, 5c, 5d, 5e, and 5f) are those portions that are associated with the imprint-fabricated ribbons 101.

The conductor or semiconductor active layer 302 can be fabricated to a thickness of a single, or a few, atoms or crystals. Therefore, the deposited thickness of the upper silicon layer on top of the substrate can determine the nano-scale thickness of the imprint-fabricated ribbons 101. The nano-scale width of the imprint-fabricated ribbons 101 can be produced using IL technology as described below relative to FIGS. 5a, 5b, 5c, 5d, 5e, and 5f. As such, IL can be used to control the width of the traces. Consequently, imprint-fabricated ribbons 101 can be produced that are nano-scale in two dimensions (thickness and width).

The semiconductor or conductor layer deposited on the substrate can be as thin as desired. By using a substrate coated with the semiconductor or conductor layer (e.g., having a nano-scale thickness), the thickness of the deposited semiconductor or conductor layer controls the final thickness of the imprint-fabricated ribbon. The thickness (height) of the imprint-fabricated ribbon 101 can therefore be decreased to nano-scale by process or material selection. As such, imprint-fabricated ribbons 101 can be fabricated in nano-scale in two dimensions (thickness and width).

Another example of an effectively thin substrate would be a shallow-implanted or shallow-doped substrate. The thin surface layer provides substantially higher electrical conductance compared to the lightly doped underlying material. Here the thickness of the dopant concentration provides effective nano-scale thinness.

IL also provides for fabrication of an imprint-fabricated ribbon 101 on such traditional semiconductor substrates as silicon, gallium arsenide, silicon-on-insulator, etc. that are typically structurally rigid. Alternatively, another embodiment of the substrate includes a non-semiconductor based substrate that is selected based on the specific properties of the substrate material (e.g., flexibility, dimension, cost, durability, etc.). The substrates supporting the semiconductor devices can include a wide variety of flexible and/or conformal substrates wherein the substrate could be bent to adapt to the specific application. Examples of flexible substrates 306 include certain plastics, metal foil, paper, and fabric. Examples of rigid substrates include certain plastics, glass, metals, etc. As such, a wide variety of substrates is considered to be within the scope of the present disclosure.

Devices and circuits can be deposited on flexible substrates to be made to, for instance, precisely shape a device, circuit, or array around such complex geometries as a human skull, other body portion, or other irregularly shaped object. By fabricating such devices on flexible substrates, it becomes possible to more precisely shape, for example, dense sensor arrays in such unusual positions and shapes as around a patient's head, arm, mouth, or other body parts to provide a more thorough and sensitive detection.

Patterning the imprint-fabricated ribbons 101 using IL provides a systematic, precise, and predefined approach that allows imprint-fabricated ribbons 101 of precisely controllable cross-sectional dimensions to be produced with a number of materials.

Improved sensitivity, selectivity, resolution, and response can result using the imprint-fabricated ribbons 101 of the desired dimensions, electrical characteristics and material. For instance, different embodiments of electric sensors can be used to sense electric resistance, electric capacitance, or electric impedance.

The narrow line width of the imprint-fabricated ribbon 101 provides a high surface-to-volume ratio, which is useful for rapid, sensitive transducer action together with small device size and low power consumption. The high surface-to-volume ratio enhances the sensitivity of a sensor incorporating the imprint-fabricated ribbon, especially when the imprint-fabricated ribbon is fabricated to nano-scale dimensions. By using IL, lines of sub-optical width can be produced in a manufacturable manner down to a cross-sectional dimension of 20 nm (nanometers) or smaller. Other readily manufacturable techniques can not produce a chemical sensor architecture having these small dimensions.

The length and the cross section of the imprint-fabricated ribbon 101 is a factor in the imprint-fabricated ribbon's electrical resistance. The imprint-fabricated ribbon's 101 resistance is related to its ability to carry a current.

Figure 4:
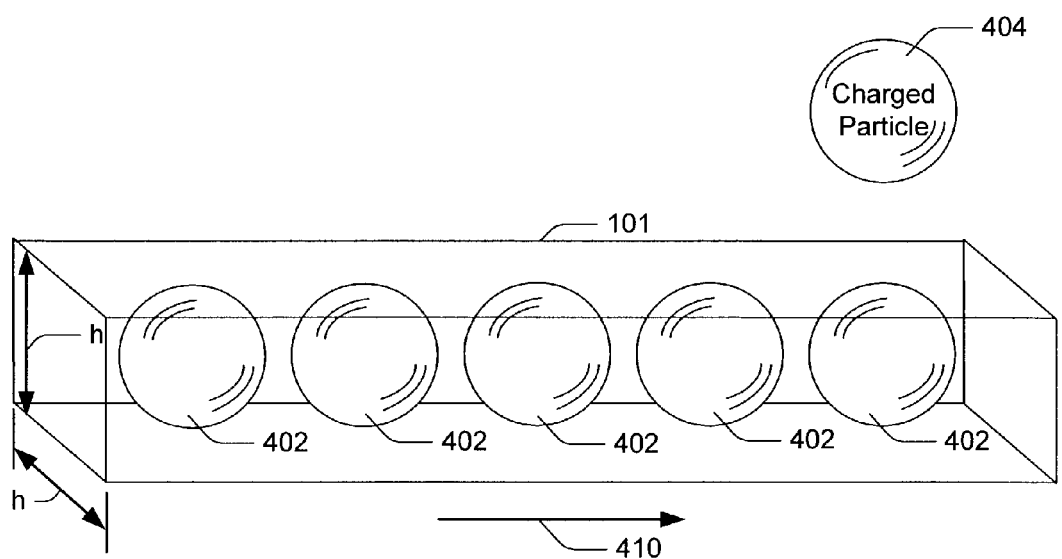
FIG. 4 is a perspective view of an electric current formed from electrons and/or holes passing through one of the imprint-fabricated ribbons as illustrated in FIGS. 1 and 2.

For instance, as illustrated in FIG. 4, as one or both of the cross-sectional dimensions of the imprint-fabricated ribbon 101 are scaled down, the imprint-fabricated ribbon dimensions approach the dimension of individual atoms. The electrons and/or holes 402 are then constrained to pass through the imprint-fabricated ribbon 101 in series (each electron and/or hole following the prior charged particle in lock-step fashion) in a direction indicated by the arrow 410. When an external electrical field associated with the charged particle 404 is brought close to this series flow of electrons and/or holes 402, one electron and/or hole can become perturbed or localized (stuck at one location). This single perturbed electron and/or hole 402 can effect (i.e., block) the entire series flow of electrons and/or holes 402 flowing in a direction 410 through the imprint-fabricated ribbon 101. This configuration therefore provides an extremely sensitive technique for adjusting the resistance of the imprint-fabricated ribbon 101 as a function of small perturbations in the charged particles 404 contained within the surrounding sample.

The cross-section of one or both dimensions of the imprint-fabricated ribbon 101 can also be scaled up from the dimensions shown in FIG. 4. In this case, a very small number of electrons and/or holes (instead of one in series) pass through the imprint-fabricated ribbon 101 both in series and in parallel. The concept that imprint-fabricated ribbons 101 provide for improved sensitivity however remains similar in that perturbations to even a small number of electrons and/or holes can magnify the effect on the total electron flow and/or hole flow within the ribbons.

The imprint-fabricated sensor 100 can be used to sense a variety of liquids, air particulates, or gasses, all by using a single imprint-fabricated ribbon 101. There are some detailed relationships between the size of the charged particle to be detected and the charge on that charged particle.

On a substrate surface, an imprint-fabricated ribbon 101 can be fabricated having a minimum width of approximately 10 nm. 500,000 nm may be the practical upper limit for the width of the imprint-fabricated ribbon. The final nano-scale line-width structure is particularly applicable to transducer elements that have to be fabricated in a variety of configurations for slightly different applications, such as in biological or chemical sensors.

Figure 5A:
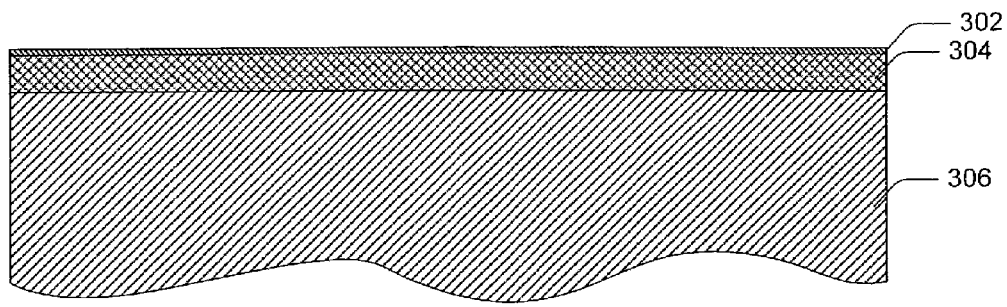
FIGS. 5a, 5b, 5c, 5d, 5e, and 5f illustrate one embodiment of a technique that can be used to fabricate one or more of the imprint-fabricated ribbons.

One embodiment of a process flow for IL is now described relative to FIGS. 5a, 5b, 5c, 5d, 5e, and 5f. FIG. 5a illustrates a typical substrate 306 (such as the SOI substrate 306), on which active layer 302 and insulator layer 304 are deposited as described relative to FIG. 3. The conductor or semiconductor active layer 302, in actuality, can be extremely thin since the depth of the layer determines the final thickness of the imprint-fabricated ribbon 101. The substrate 306 provides support for the fragile layers 302 and 304. Though 302, 304, and 306 are illustrated in the SOI configuration, any other configuration that provides suitable support for the conductor or semiconductor active layer 302 formed from an electrical semiconductor or an electrical conductor may be used.

Figure 5B:
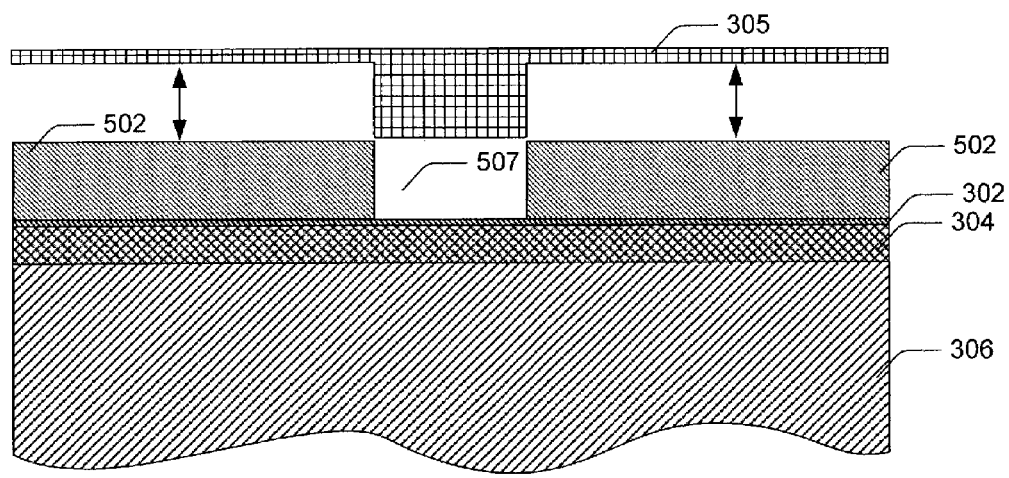

In FIG. 5b, an imprint layer 502 is added above the conductor or semiconductor active layer 302. In one embodiment, the imprint layer is a polymer. The imprint layer 502 is then imprinted (or stamped) using IL techniques to form desired grooves 507 within the imprint layer 502. Using IL techniques, the imprint layer 502 is imprinted or stamped using an imprint template or mold 305 (as shown in FIG. 5b). The contour of the imprint template or mold is replicated into the imprint layer. The pattern contour 507 closely follows the patterns of the electric circuitry required by the configuration of the imprint-fabricated sensor 100. As such, the regions of the imprint layer 502 that are stamped correspond to the regions of the conductor or semiconductor active layer 302 that eventually form the imprint-fabricated ribbons 101 and the associated electronic circuitry.

Two embodiments of imprint lithography techniques are within the intended scope of imprint lithography as described in the present disclosure, and are "thermal imprint lithography" and "step and flash imprint lithography". In "step and flash" imprint lithography, the imprint layer 502 is selected to have photochemical properties (e.g., include a photoresist), and the imprint template is optically transparent so light can be applied to the imprint layer. The inverse topographical pattern (i.e., grooves or trenches 507 that can have a width in the nanoscale range) can be formed in the imprint layer at substantially lower temperatures and/or pressures with "step and flash" imprint lithography than with "thermal imprint" lithography by exploiting the photochemical conversion and curing of the imprint layer 502 that occur at relatively low temperatures.

Thermal imprint lithography and step and flash imprint lithography rely on different mechanisms to form the topographical patterns 507 in the imprint layer 502 which, in turn, are based on the topographical patterns 507 formed in the imprint template 305. Any type of IL described in this disclosure can use thermal IL or step and flash IL.

Thermal IL relies primarily on: a) heat applied to the imprint layer 502, and b) pressure applied from the imprint template 305 into the imprint layer 502. To provide the imprinting process, the imprint template 305 (having the inverse pattern of grooves or trenches 507 from those required in the final article) is forced into, and forms corresponding patterns in, imprint layer 502. The imprint template 305 can be formed using e-beam lithographic techniques that are applied only once for each master-imprint template. For imprinting, the imprint template 305 is typically pressed into the imprint layer 502 at some pressure and at temperatures moderately higher than room temperature.

Step and flash IL relies on light (e.g., ultraviolet light) transmitted through the imprint template 305 into the imprint layer as the imprint template 305 contacts the imprint layer 502. Applying light into such imprint layer materials as a polymer hardens or cures the polymer into its desired configuration. In step and flash IL, sufficient pressure is applied from the imprint template 305 to shape the material of the imprint layer prior to the application of the light. The light that is transmitted through the imprint template 305 into the imprint layer 502 is at a frequency (e.g., ultraviolet for certain imprint layer materials) that can modify the photoresist polymer materials forming the imprint layer (e.g., by cross-linking).

The imprint template 305 used in step and flash IL is thus light-transparent so light can be directed through the imprint template 305 into the material forming the imprint layer 502. In one embodiment, the imprint template 305 used in step and flash IL is made from quartz that can be etched using, for example, e-beam lithography. There is no requirement that the imprint template in thermal IL be light transparent.

In thermal IL, the imprint template 305 is able to withstand the elevated temperatures required to soften the material forming the imprint layer 502. They may be, for example, made from a semiconductor such as silicon. There is no requirement in step and flash IL that the imprint template 305 be able to withstand such elevated temperatures since raised temperatures are not used. Performing step and flash IL at non-elevated temperatures can be useful for fabrication of multi-layered structures because raising the temperature of an upper-most layer to a temperature where it becomes deformable may also have the effect of causing underlying layers to reach a temperature where they are either deformable, or are close to being deformable. If the lower layers are at a temperature at or near where they are deformable, then the pressures applied by the stamping or imprinting actions of imprint lithography on the upper layer (to form the grooves and trenches of the inverse topographical patterns) may act to deform features on the buried lower layers.

As such, during thermal IL, the temperatures of the substrate and the imprint layers must be closely monitored. With step and flash IL, the lower layers, following curing, are maintained at a relatively low temperature so that the multiple deposited layers will continue to be solid. In addition, step and flash IL does not require the time to heat up, and then cool, the imprint layer during each cycle. Therefore, taller structures often can be built using step and flash IL as compared with structures built using certain other lithographic techniques (since the previously deposited layers are not raised to temperatures sufficient to cause distortion in the previously deposited layers).

The temperature of the imprint layer 502 during thermal IL is sufficiently high to make the material of the imprint layer 502 somewhat deformable and conform to the shapes and patterns formed in the imprint template 305. The amount of force necessary to drive the topographical patterns 512 of the imprint template into the material of the imprint layer 502 varies depending on the selected material (i.e., polymer or non-polymer) in the imprint layers and the configurations in the imprint template. For thermal imprint IL, the imprint layer is cooled to a temperature that it no longer has deformable characteristics once the imprint template 305 has been driven downward into the material of the imprint layer to form the grooves or trenches. For step and flash IL, light is directed through the imprint template 305 until the imprint layer 502 is cured.

Figure 5C:
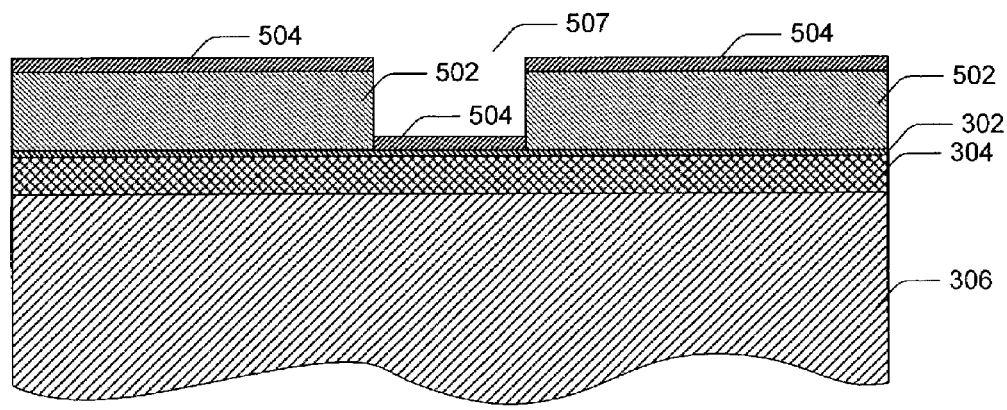
Figure 5D:
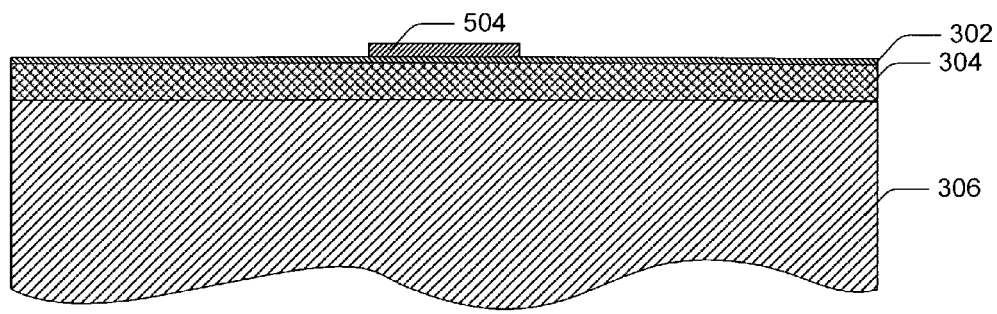

In FIG. 5c, one or more metal layers 504 are deposited on the upper surface (including both the imprinted and non-imprinted portions) of the imprint layer 502 and/or the conductor or semiconductor active layer 302 following the imprinting shown in FIG. 5b. In one embodiment, the metal layer 504 includes a plurality of layers (e.g., 5 nm Ti, and 10 nm Al). In FIG. 5d, the remaining imprint layer 502 and the portions of the metal layer 504 above the imprint layer 502 are "lifted off" to be separated from the conductor or semiconductor active layer 302.

Following lift-off, the portions of the active layer 302 under the lifted-off portions of the imprint layer 502 in FIG. 5c are exposed as shown in FIG. 5d. Those portions of the metal layer 504 that are directly in contact with the conductor or semiconductor active layer 302 following FIG. 5c remain in contact with the conductor or semiconductor active layer 302 following FIG. 5d.

Figure 5E:
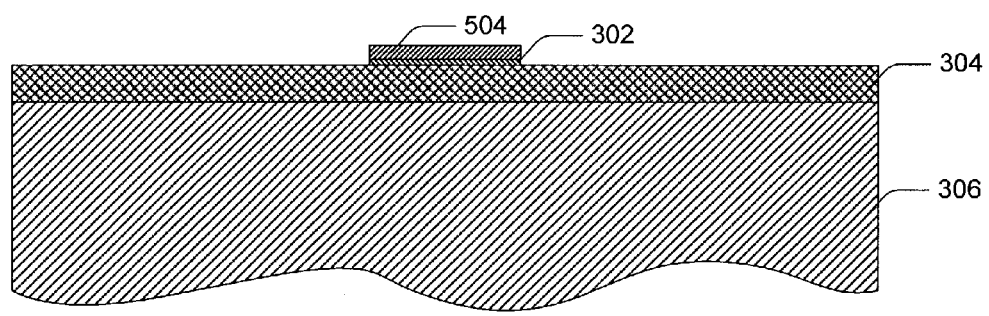

In FIG. 5e, the substrate undergoes reactive ion etching (RIE). Those portions of the conductor or semiconductor active layer 302 that are under the remaining portions of the metal layer 504 remain in place following the RIE. Those portions of the conductor or semiconductor active layer 302 that are exposed (i.e. not under the metal layer) are etched away following the RIE. The RIE does not etch an appreciable thickness (depth) of the insulator layer 304. Other known etching techniques (such as wet chemical etching) may be used, and are within the scope of the present disclosure.

Figure 5F:
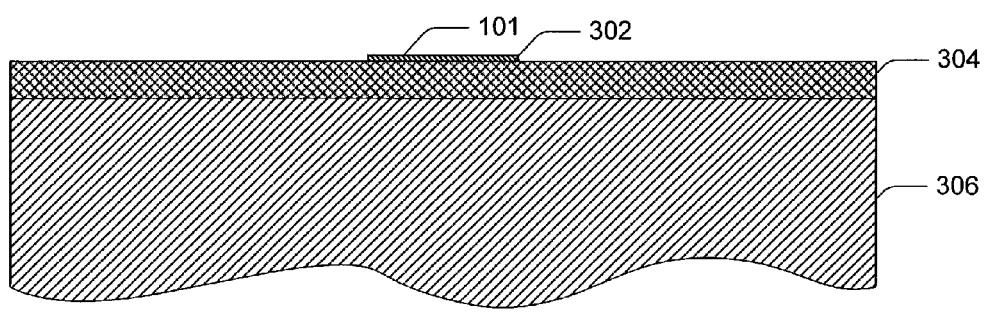

In FIG. 5f, the substrate undergoes chemical etching to remove the remaining portions of the metal layer 504. This etching therefore leaves the conductor or semiconductor active layer 302 exposed. Those portions of the conductor or semiconductor active layer 302 that remain following FIG. 5f form the imprint-fabricated ribbons 101 (and the associated conductor or semiconductor portions) following IL.

Using IL as illustrated in FIGS. 5a, 5b, 5c, 5d, 5e, and 5f offers several advantages, including the ability to define and produce an array of imprint-fabricated ribbons 101. IL can produce nanostructures, microstructures, macrostructures, and even macrostructures that are orders of magnitude larger, simultaneously. IL can perform the integration between imprint-fabricated ribbons 101 having different sizes effectively and efficiently. Another important advantage of the simultaneous fabrication of nano-structures, micro-structures, and macro-structures is that the technical performance of the part may vary with size; such that the optimal size might vary between applications. The usage of IL renders a two-dimensional pattern of features, either one of which is extensible down to the nano-scale. The third dimension can be as large as desired since that dimension is the "length" of the imprint-fabricated ribbons 101.

One technique to fabricate an imprinted sensor (such as may be used as a chemical and/or biological sensor) on a SOI substrate 306 by using IL with other processing methods follows. The top conductor or semiconductor active layer 302 may also include dopants (e.g., applied using ion implantation).

The substrate 306 is covered with the imprint layer 502 including a thin resist such as, e.g., a polymer. During IL, impressions 507 are stamped in the imprint layer 502 as shown in FIG. 5b. The pattern of impressions in the metal layer 504 correspond to the final pattern in the conductor or semiconductor active layer 302 forming the elongated imprint-fabricated ribbon 101 as shown in FIG. 5f. The final pattern imprint-fabricated ribbon ideally includes the contact points 104, 106, 108, 110, 120, and 122 as described.

In FIG. 5c, the metal layer 504 such a tin or aluminum is deposited on the thin imprint layer 502. The metal layer is deposited in the impression portion of the imprint layer that followed the stamping/imprinting process shown in FIG. 5b. Following a procedure called "lift-off" (of the remaining portions of the thin imprint layer 502), the thin imprint layer 502 is removed with the attached metal layers. The deposited material that remains within the stamped/imprinted layer 502 shown following the lift-off shown in FIG. 5d acts as a hardmask material to resist etching of material under the hardmask material. Reactive ion etching (RIE), or other types of dry etching, is performed as shown in FIG. 5e, which thins the substrate 306 by etching away the conductor or semiconductor active layer 302 at those locations that correspond to where the hard mask of the metal layer 504 has been removed following lift-off. The prior pattern of impressions 507 (caused by stamping of the thin imprint layer 502 as shown in FIG. 5b) result in protrusions arranged as the final pattern in the conductor or semiconductor active layer 302 that is formed on the upper surface of the substrate 306 as shown in FIG. 5f.

The thickness of the dry-etch (i.e., resulting from the RIE as shown in FIG. 5e) corresponds to the vertical thickness of the protrusions forming the conductor or semiconductor active layer 302 as shown in FIG. 5f. By selecting the thickness of the imprint-fabricated ribbons 101 to match the thickness of the original active silicon (e.g., silicon or SOI) layer, the imprint-fabricated ribbon 101 is fabricated whose line height is pre-determined. Such thickness determination results primarily from the deposited thickness of the conductor or semiconductor active layer 302 on the wafer or substrate 306. In one embodiment, the imprint-fabricated ribbon 101 forms a transducer element. To be most useful in transducer embodiments, the upper surface of the imprint-fabricated ribbon 101 is designed or engineered to provide for enhanced chemical sensitivity.

The insulator layer 304 is formed, for example, as a thin surface layer of silicon dioxide. In some cases, the silicon dioxide provides a surface for chemical and/or biological functionalization. The silicon dioxide layer may also provide passivation against chemical attack. Such surface functionalization can be performed via inorganic or organic species, including biochemicals or antigens, for example. Chemical and/or biological absorption perturbs the electrical conductance of the imprint-fabricated ribbons 101, and can be sensed by resistance measurements. To facilitate electrical measurement, the imprint-fabricated ribbons have conducting electrical contact points at either end, that are arranged either in a two-point resistance measurement configuration or a four-point resistance measurement configuration.

The operational mode of measurement may also include a front gate (not shown) and a back-gate. The back-gate biases the substrate 306 via another terminal 308 (e.g., on the bottom of the substrate 306 as shown in FIG. 3). Such biasing of the back-gate has the effect of modifying the electron density that is available in the ribbon, which often behaves much like modifying a field effect in a MOS transistor. The usage of imprint lithography to fabricate imprint-fabricated ribbons can also accommodate the co-fabrication of non-ribbon-like imprint-fabricated structures, which is desirable to provide additional functionality, such as the backgate contact.

In one embodiment, the imprint-fabricated ribbons 101 are in intimate contact with the substrate and their cross-section is predominantly square, rectangular or trapezoidal. The cross sectional configuration depends on such factors as the width of the imprint-fabricated ribbons 101, the thickness of the conductor or semiconductor active layer 302, and even certain aspects of the dry (RIE) etch process which may render vertical or slanted side walls of the conductor or semiconductor active layer 302. The longer dimension of rectangular imprint-fabricated ribbons 101 can be arranged to extend either horizontally or vertically, depending on the fabrication configuration and process. It is unlikely that the conductor or semiconductor active layer 302 forming the imprint-fabricated ribbons 101 will have a circular or oval cross-section (such as certain prior-art loose tubular wires for example), since such a cross-sectional configuration is not a likely shape to be produced using IL. Providing substantially rectangular and/or trapezoidal imprint-fabricated ribbons 101 allows for relatively easy calculation of the dimensions and the electrical resistance of the imprint-fabricated ribbons. Even though oval, circular, or other configurations are difficult to provide using IL techniques, it is possible to provide a variety of non-rectangular or trapezoidal configurations. Any of the substantially rectangular, trapezoidal, or other configurations are within the intended scope of the imprint-fabricated ribbons of the present disclosure, as long as IL is being used to fabricate the imprint-fabricated ribbons.

There are variations of the IL process that are used to form the imprint-fabricated ribbons 101. One embodiment of IL process would be to fill the IL impressions in the resist imprint layer 502 with another material that is itself an electrical transducer of chemical adsorption. Examples of materials that can be used to form the imprint-fabricated ribbons 101 include palladium, that may be used to detect hydrogen; amorphous or polycrystalline silicon, that could be used as field-effect devices similar to the above SOI silicon example; and metal-oxides such as tin-oxide, titanium-oxide, or vanadium-oxide. The metal-oxide imprint-fabricated ribbons 101 can function as chemical sensor elements using the above fabrication techniques.

There are many application opportunities afforded by imprint-fabricated ribbons. For example, FIG. 6 illustrates the creation of an array 600 of sensor structures for serial or parallel usage depending on how they were functionalized. The array 600 of the imprint-fabricated ribbons 101 that form the imprint-fabricated sensors 100 can be interconnected. There are, in fact, a variety of embodiments of interconnected arrayed sensors known in applications involving the control and sensing of electric potential supplies.

An imprint-fabricated sensor configured with imprint-fabricated ribbons can be beneficially used in many applications that require highly sensitive analysis of a non-solid material or sample. In this disclosure, imprint-fabricated ribbons are described that exploit the technical advantages of previous nano-scale wire methods (high sensitivity, selectivity, and resolution) but provide a systematic method for patterning and organizing the arrays of imprint-fabricated ribbons 101 using IL. Furthermore, the methods that are described herein provide a technique to tailor or tune the electrical and chemical properties of the imprint-fabricated ribbon 101 thereby optimizing it's performance and making a more "manufacturable" article. The advantages provided by this invention can lead to useful, manufacturable arrays of imprint-fabricated ribbons 101 as illustrated in FIG. 6. It is emphasized that electronic control circuitry that is applied to such electronic devices as arrays of sensors, multiplexers, demultiplexers, etc. is generally known and is within the intended scope of the present disclosure.

Figure 7:
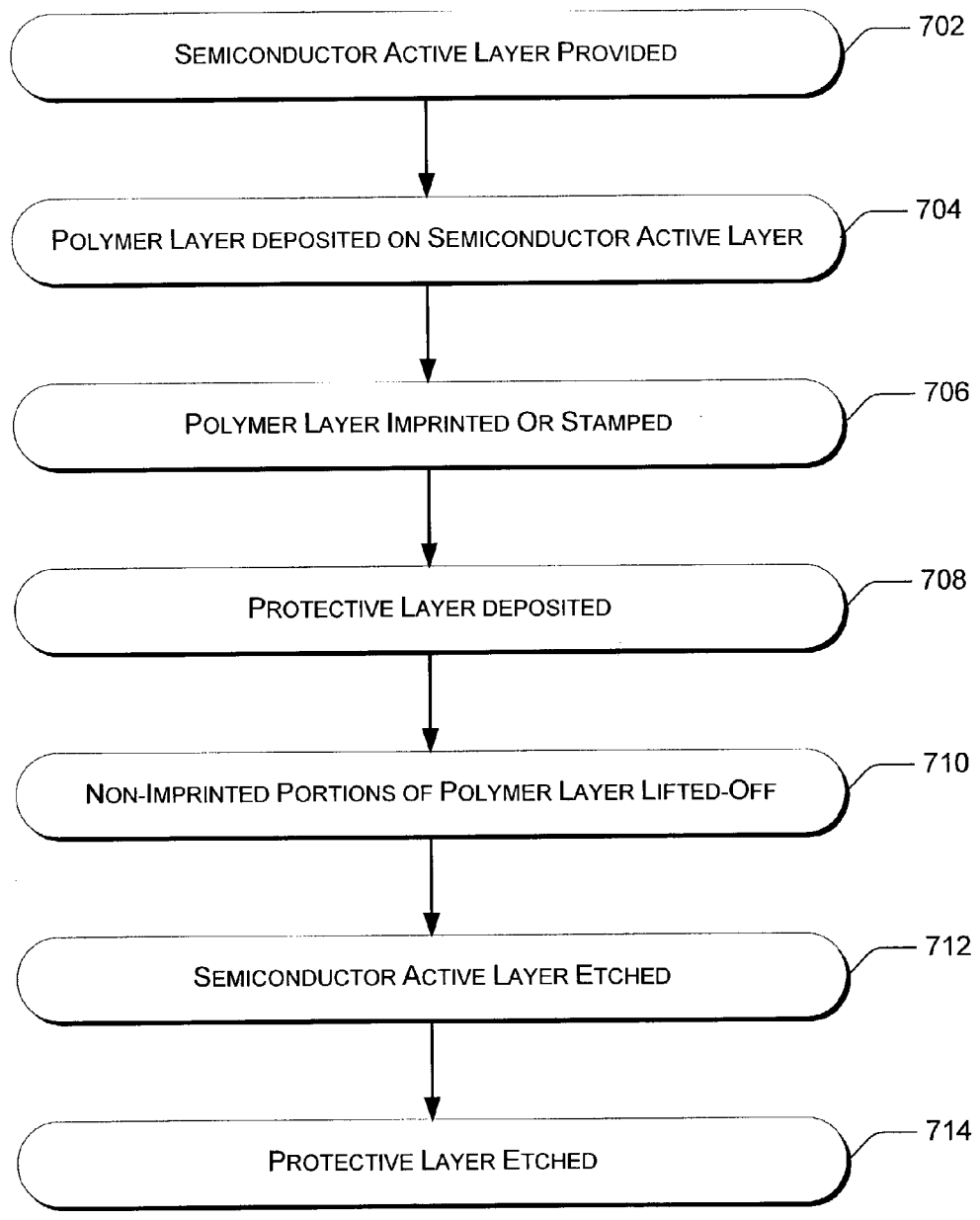
FIG. 7 illustrates a flow chart of one embodiment of a process that can be used to fabricate the imprint-fabricated ribbons such as illustrated in FIGS. 5a, 5b, 5c, 5d, 5e, and 5f.

FIG. 7 illustrates one embodiment of process 700 that is used to form the imprint-fabricated ribbons 101 as shown in FIGS. 5a, 5b, 5c, 5d, 5e, and 5f. The process 700 includes 702 in which a semiconductor active layer having a prescribed thickness is located as provided in FIG. 5a. Typically the semiconductor active layer is provided by depositing the semiconductor active layer onto a substrate. The process in 704 deposits an imprint layer 502 on the semiconductor active layer (as illustrated in FIG. 5*b*). In 706, the imprint layer 502 is imprinted or stamped to yield both imprinted, and non-imprinted, portions of the imprint layer 502 (as also shown in FIG. 5*b*). In 708, a protective layer (i.e., a metal layer) is deposited on both the imprinted, and the non-imprinted, portions of the imprint layer 502 as shown in FIG. 5*c*. The protective layer forms a hard mask that protects the material under the hard mask from further etching. The non-imprinted portions of the imprint layer 502 (including those portions of the protective layer deposited on the non-imprinted portions of the imprint layer) are lifted-off in 710 as shown in FIG. 5*d*. The semiconductor active layer is etched in 712 as shown in FIG. 5*e*, wherein those portions of the semiconductor active layer that are below the remaining protective layer following lift-off are not etched, while those portions that are not below are etched. In 714, the remaining portions of the protective layer (e.g., metal layer) following the lifting-off that is deposited in 708 is etched, yielding the imprint-fabricated ribbons 101 as shown in FIG. 5*f*.

Figure 9:
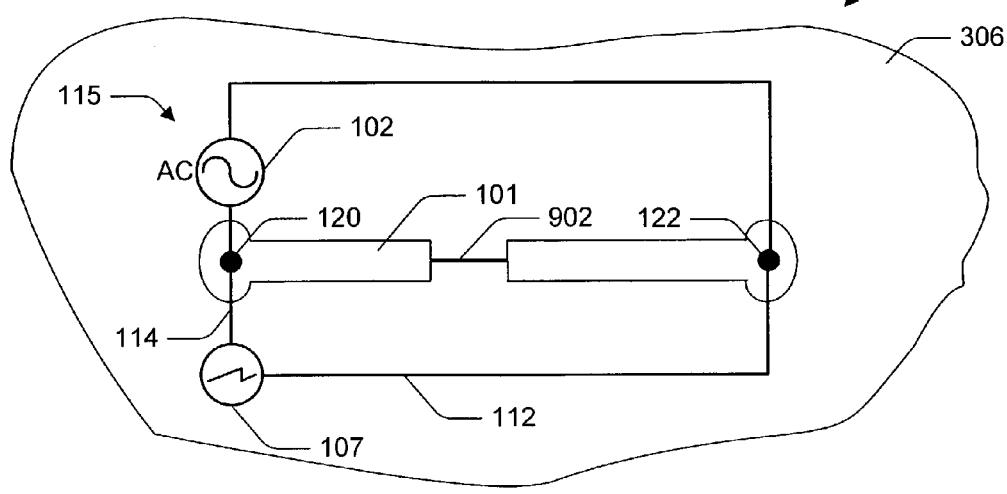
FIG. 9 shows another embodiment of imprint fabricated ribbon from that shown in FIG. 2.

FIG. 9 illustrates an altered embodiment of imprint-fabricated ribbon 101 from that illustrated in FIG. 1. The FIG. 9 embodiment of the imprint-fabricated ribbon 101 includes a step-down region 902 is narrower than the remainder of the imprint-fabricated ribbon. In certain embodiments, the step-down region can be in the range of nanometers or tens of nanometers. Using the step-down region 902 can result in a significantly increased electrical resistance compared to that of an imprint-fabricated ribbon 101 without the step-down region. The remainder of the ribbon, in fact, is so much larger than the step-down region 902 that it may be considered as having negligible electrical resistance as compared to the step-down region. The use of a step-down region 902 allows for a relatively small portion of the imprint-fabricated region 101 to be configured to provide the desired electrical characteristics of the overall part. As such, the imprint fabricated ribbons can be produced and used in a large variety of configurations and applications that can be readily, accurately, and cost effectively produced.

Figure 8:
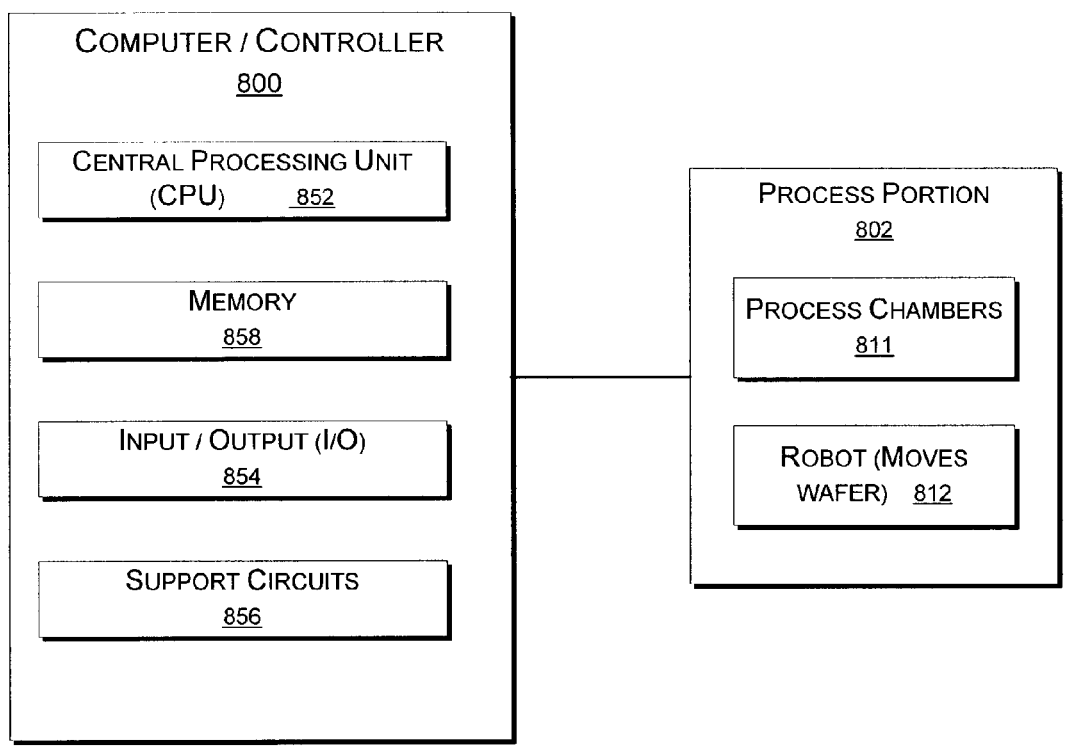
FIG. 8 shows a block diagram of one embodiment of a computer or controller that can control the operation of the process illustrated in FIG. 7.

FIG. 8 illustrates one embodiment of a controller or a computer 800 that can perform method 700 to create the imprint-fabricated ribbons 101 on the substrate 306 illustrated in FIG. 3, using the technique illustrated in FIGS. 5*a*, 5*b*, 5*c*, 5*d*, 5*e*, and 5*f*. A process portion or "fab" is illustrated as 802. The process portion 802 may include a variety of process chambers 811 between which the substrate 306 is translated, often using a robot mechanism 812. The particulars of the processing varies with the depth of materials that are deposited and then etched, the pattern being imprinted and then etched using IL and, often, even varies between different suppliers. Such processes as chemical vapor deposition, physical vapor deposition, electro-chemical deposition, and reactive ion etching (RIE) are known for depositing and/or etching specific materials within the process portion 802.

The controller or the computer 800 comprises a central processing unit (CPU) 852, a memory 858, support circuits 856 and input/output (I/O) circuits 854. The CPU 852 is a general purpose computer which when programmed by executing software 859 contained in memory 858 becomes a specific purpose computer for controlling the hardware components of the processing portion 802. The memory 858 may comprise read only memory, random access memory, removable storage, a hard disk drive, or any form of digital memory device. The I/O circuits comprise well known displays for the output of information and keyboard, mouse, track ball, or input of information that can allow for programming of the controller or computer 800 to determine the processes performed by the process portion 802 (including the associated robot action included in the process portion). The support circuits 856 are well known in the art and include circuits such as cache, clocks, power supplies, and the like.

The memory 858 contains control software that, when executed by the CPU 852, enables the controller or the computer 800 to digitally control the various components of the process portion 802. A detailed description of the process that is implemented by the control software is described with respect to FIG. 6, as illustrated with respect to FIGS. 5*a*, 5*b*, 5*c*, 5*d*, 5*e*, and 5*f*. In another embodiment, the computer or controller 800 can be analog. For instance, application specific integrated circuits are capable of controlling processes such as occur within the process portion 802.

Although the invention is described in language specific to structural features and methodological steps, it is to be understood that the invention defined in the appended claims is not necessarily limited to the specific features or steps described. Rather, the specific features and steps disclosed represent preferred forms of implementing the claimed invention.

What is claimed is:

1. A method comprising:
fabricating an imprint-fabricated ribbon using imprint lithography, including integrating the imprint-fabricated ribbon in an imprint fabricated sensor, by:
providing a semiconductor active layer having a prescribed thickness on a substrate,
depositing an imprintable layer on the semiconductor active layer,
imprinting the unprintable layer in the pattern of an imprint-fabricated ribbon to create imprinted portions of the imprintable layer and non-imprinted portions of the imprintable layer,
depositing a protective layer on both imprinted portions of the imprintable layer and non-imprinted portions of the imprintable layer,
removing the non-imprinted portions of the imprintable layer from the substrate, wherein the non-imprinted portions include those portions of the protective layer deposited on the non-imprinted portions of the imprintable layer, and
etching the semiconductor active layer, wherein those portions of the semiconductor active layer that are below the remaining protective layer following lift-off are substantially not etched, while those portions of the semiconductor active layer that are not below the remaining protective layer following lift-off are substantially etched.

2. The method of claim 1, wherein the imprint-fabricated ribbon is then functionalized.

3. The method of claim 2, wherein the functionalized is by fabrication of a dielectric layer such as silicon oxide or nitride that can be readily protonated or deprotonated for the detection of protons in solution.

4. The method of claim 2, wherein the functionalization is by a coating of organic species.

5. The method of claim 4, wherein the organic species includes one from the group of antibodies, antigens, polymers, polynucleic acids, polypeptides, nanoparticles, or ion exchange membranes.

6. The method of claim 1, wherein the protective layer includes a metal.

7. The method of claim 1, wherein the protective layer includes a non-metal.

8. The method of claim 1, wherein the protective layer is removed following the etching.

9. The method of claim 1, wherein chemical etching acts to remove the protective layer.

10. The method of claim 1, wherein the etching includes reactive ion etching (RIE).

11. The method of claim 1, wherein the imprinting the unprintable layer includes a stamping process.

12. The method of claim 1, wherein imprint lithography is used to fabricate the imprint-fabricated ribbon.

13. The method of claim 1, wherein the imprint-fabricated ribbon is fabricated on a Silicon-On-hisulator (SOD) substrate.

14. The method of claim 1, wherein the prescribed thickness is selected to provide a nano-scale thickness of the imprint-fabricated ribbon.

15. The method of claim 1, wherein a prescribed width is selected to provide a nano-scale width of the imprint-fabricated ribbon.

16. The method of claim 15, wherein the imprinting of the imprintable layer at least partially provides for the prescribed width of the imprint-fabricated ribbon.

17. The method of claim 15, wherein the deposition of a protective layer on both imprinted portions of the imprintable layer and non-imprinted portions of the imprintable layer at least partially provides for the prescribed width of the imprint-fabricated ribbon.

18. The method of claim 15, wherein the prescribed width is greater than a prescribed thickness of the imprint-fabricated ribbon.

19. The method of claim 15, wherein the prescribed width is less than a prescribed thickness of the imprint-fabricated ribbon.

20. The method of claim 15, wherein the prescribed width is substantially equal to a prescribed thickness of the imprint-fabricated ribbon.

21. The method of claim 1, which is at least partially performed by a general purpose computer.

22. The method of claim 1. wherein the imprint-fabricated ribbon is configured for a four-point electrical resistance measurement.

23. The method of claim 1, wherein the imprint-fabricated ribbon is configured for a two-point electrical resistance measurement.

24. The method of claim 1, wherein the removing the non-imprinted portions of the imprintable layer from the substrate includes lifting off the non-imprinted portions of the imprintable layer.

25. The method of claim 1, further comprising applying electrical contacts to the imprint-fabricated ribbons.

26. A method comprising:
fabricating an imprint-fabricated ribbon using imprint lithography, including integrating the imprint-fabricated ribbon in an imprint fabricated sensor, by:
providing a conductor active layer having a prescribed thickness,
depositing an imprintable layer on the conductor active layer,
imprinting the imprintable layer,
depositing a protective layer on both imprinted portions of the imprintable layer and non-imprinted portions of the imprintable layer,
removing those non-imprinted portions of the imprintable layer including those portions of the protective layer deposited on the non-imprinted portions of the imprintable layer, and
etching the conductor active layer, wherein those portions of the conductor active layer that are below the remaining protective layer following lift-off are not etched; and
applying the imprint-fabricated ribbon to contact an analyte, wherein the imprint-fabricated ribbon is configured to perform sensing of target molecules contained in the analyte.

27. The method of claim 26, wherein the configuring of the imprint-fabricated ribbon includes functionalization to promote the adsorption of certain species in lieu of others.

28. The method of claim 26, wherein the protective layer includes a metal.

29. The method of claim 26, wherein the protective layer is removed following the etching.

30. The method of claim 29, wherein chemical etching acts to remove the protective layer.

31. The method of claim 26, wherein the etching includes reactive ion etching (RIE).

32. The method of claim 26, wherein the imprinting the imprintable layer includes a stamping process.

33. The method of claim 26, wherein the imprint-fabricated ribbon is fabricated on a Silicon-On-Insulator (SOI) substrate.

34. The method of claim 26, wherein the prescribed thickness is selected to provide a nano-scale thickness of the imprint-fabricated ribbon.

35. The method of claim 26, wherein a prescribed width is selected to provide a nano-scale width of the imprint-fabricated ribbon.

36. The method of claim 35, wherein the imprinting of the imprintable layer at least partially provides for the prescribed width of the imprint-fabricated ribbon.

37. The method of claim 36, wherein the depositing a protective layer on both imprinted portions of the imprintable layer and non-imprinted portions of the imprintable layer at least partially provides for the prescribed width of the imprint-fabricated ribbon.

38. The method of claim 26 which includes step and flash imprint lithography.

39. The method of claim 26 which includes thermal imprint lithography.

40. The method of claim 26, further comprising transducing a chemical event to an electrical signal.

41. The method of claim 26, further comprising transducing a biological event to an electrical signal.

42. The method of claim 26, further comprising applying electrical contacts to the imprint-fabricated ribbons.

43. The method of claim 26, wherein the imprint-fabricated ribbon is extendible down to the nanoscale in one cross-sectional dimension.

44. The method of claim 26, wherein the pattern of the imprint-fabricated ribbon includes a simple line segment.

45. The method of claim 26, wherein the pattern of the imprint-fabricated ribbon includes one from the group of a serpentine, an hourglass figure, a forked shape, or a dog-bone shape.

46. The method of claim 26, wherein the imprinting of the imprintable layer is executed concurrently over the entire pattern.

47. The method of claim 26, wherein the substrate is flexible.

48. The method of claim 47, wherein the imprint-fabricated ribbon is formed on a thin film portion is deposited on the substrate.

49. The method of claim 26, wherein the imprint-fabricated ribbon is then functionalized.

50. The method of claim 49, wherein the functionalizing is by fabrication of a dielectric layer such as silicon oxide or nitride that can be readily protonated or deprotonated for the detection of protons in solution.

51. The method of claim 49, wherein the functionalization is by a coating of organic species.

52. The method of claim 51, wherein the organic species includes one from the group of antibodies, antigens, polymers, polynucleic acids, polypeptides, nanoparticles, or ion exchange membranes.

* * * * *

UNITED STATES PATENT AND TRADEMARK OFFICE
CERTIFICATE OF CORRECTION

PATENT NO.        : 7,410,904 B2
APPLICATION NO. : 10/423063
DATED             : August 12, 2008
INVENTOR(S)       : James Stasiak et al.

It is certified that error appears in the above-identified patent and that said Letters Patent is hereby corrected as shown below:

In column 16, line 33, in Claim 1, delete "unprintable" and insert -- imprintable --, therefor.

In column 17, line 8, in Claim 11, delete "unprintable" and insert -- imprintable --, therefor.

In column 17, line 12, in Claim 13, delete "Silicon-On-hisulator (SOD" and insert -- Silicon-On-Insulator (SOI) --, therefor.

In column 17, line 39, in Claim 22, delete "claim 1." and insert -- claim 1, --, therefor.

Signed and Sealed this

Eighteenth Day of November, 2008

JON W. DUDAS
*Director of the United States Patent and Trademark Office*